United States Patent [19]
Cortial et al.

[11] Patent Number: 5,228,889
[45] Date of Patent: Jul. 20, 1993

[54] DEVICE FOR ELIMINATING BUBBLES OF GAS IN A FLOWING LIQUID

[75] Inventors: Jean-Loup Cortial, Lyons; Jacques Chevallet, Serezin du Rhone, both of France

[73] Assignee: Hospal Industrie, France

[21] Appl. No.: 836,841

[22] Filed: Feb. 19, 1992

[30] Foreign Application Priority Data

Mar. 1, 1991 [FR] France .................. 90 02692

[51] Int. Cl.⁵ .............................. B01D 19/00
[52] U.S. Cl. ............................ 55/160; 55/164; 55/199; 55/203
[58] Field of Search ............. 55/160, 164, 170, 199, 55/203, 461; 210/436, 472

[56] References Cited

U.S. PATENT DOCUMENTS

| | | | |
|---|---|---|---|
| 3,039,255 | 6/1962 | Van Der Meer | 55/461 |
| 3,109,714 | 11/1963 | Skeggs | 55/190 |
| 4,428,757 | 1/1984 | Hall | 55/15 |
| 4,493,705 | 1/1985 | Gordon et al. | 604/122 |
| 4,976,754 | 12/1990 | Edelstein | 55/160 |

FOREIGN PATENT DOCUMENTS 53200 6/1937 Denmark ............... 55/461

Primary Examiner—Charles Hart
Attorney, Agent, or Firm—Finnegan, Henderson, Farabow, Garrett & Dunner

[57] ABSTRACT

A device for eliminating bubbles of gas from a liquid comprises a channel of varying section for the liquid, the channel having a high point for collecting bubbles under gravity, and means for dynamically concentrating bubbles upstream from the high point, said means being constituted by a curved length of the channel situated upstream from the high point. This type of device is used in a variety of technical fields as a component in hydraulic circuits where the presence of bubbles of gas is undesirable.

16 Claims, 1 Drawing Sheet

DEVICE FOR ELIMINATING BUBBLES OF GAS IN A FLOWING LIQUID

The present invention relates to a device, commonly called a "bubble trap", for eliminating bubbles of gas in a flowing liquid.

BACKGROUND OF THE INVENTION

Bubble traps are used in a variety of technical fields as components in hydraulic circuits where the presence of bubbles of gas is undesirable. By way of example, the hydraulic circuit of apparatus used in renal dialysis for fabricating a dialysis liquid and causing it to flow through a membrane exchanger includes several bubble traps, without which the transfer rate in the exchanger would be reduced, the operation of the pumps would be disturbed, and measurements of the quantity of blood plasma ultrafiltering through the membrane, if any, would be erroneous.

In conventional manner, a bubble trap used in that type of apparatus comprises a slightly tapering vessel closed by a cover having a bulge, with a closable purge duct being connected to the top thereof. The vessel is divided into two over a portion of its height by means of a transverse partition, with liquid being let in and let out on respective opposite sides of the partition. The function of the partition is to prevent liquid that enters the bubble trap escaping therefrom immediately. The top of the bubble trap is provided with a liquid detector which is used to cause the purge duct to be opened each time that the detector no longer detects the presence of liquid. By way of example, a bubble trap of this type having an internal volume of about 150 ml can be used to extract about 4.5 ml of air (measured at atmospheric pressure) per minute from a liquid flowing at a rate of about 1200 ml/min.

The conventional bubble trap described above suffers from several drawbacks. Given its shape, the volume of air removed on each purge is relatively large, thereby disturbing the flow of the liquid, in particular at the inlet and at the outlet of the bubble trap. In addition, compared with the volume of the tubular ducting of the circuit, the volume of the bubble trap is not negligible, which means that putting the apparatus into operation (sterilization, initial filling, warming up) takes quite a long time. Finally, the bubble trap can never be completely emptied.

Patent document U.S. Pat. No. 4,493,705 describes a blood container constituted by a banana-shaped flexible bag having an inlet and an outlet that extend the central axis of the bag, and also having a vent situated at the top of the bag approximately halfway between the inlet and the outlet. Although the shape of that container causes the fluid flowing therethrough to slow down in its middle portion, it is not designed to cause eddies to disappear nor to enhance the removal of bubbles from the flowing liquid. In addition, that container requires manual intervention to empty it.

An object of the present invention is to provide a bubble trap that gives optimum performance while being of small volume and being capable of being emptied completely.

SUMMARY OF THE INVENTION

That is why the present invention provides a device for eliminating bubbles of gas from a liquid, the device comprising duct means for the liquid and having a curve at a high point to enable bubbles to collect under gravity, the duct means having a portion of flaring section upstream from the high point and a portion of tapering section downstream from the high point, together with means for dynamically concentrating the bubbles upstream from the high point. In a preferred embodiment, the means for dynamically concentrating the bubbles comprise a curved portion of the duct situated upstream from the portion of the duct which is of flaring section, said curved duct portion being of substantially constant section and having a radius of curvature that is less than the radius of curvature of the duct means at the high point. It defines an outer curved trajectory for the bubbles that runs into a top path of greatest slope in the duct means, which top path terminates at the high point.

This disposition considerably enhances elimination of any bubbles entering the bubble trap by means of a dynamic flow effect which tends to concentrate the bubbles and to expel them to the outside of the curved length, with this effect being added to that of settling under gravity. It is thus possible, for given throughput, to make bubble traps that are much smaller in volume than conventional bubble traps.

The device preferably includes gas collection means constituted by an oblong cell opening out to the duct means at the high point.

This disposition makes it possible for each purge operation to eliminate only a small quantity of gas, such that the flow of liquid through the duct means is not disturbed thereby.

The device may further include means for causing the liquid to flow substantially without eddies through the duct means. Said means comprise a profile for the duct means shaped to follow the streamline at the outlet of the curved length together with a partition at the junction between the duct means and the cell for collecting bubbles, which partition provides continuity for the duct means and includes at least one slot for passing the bubbles.

By means of this disposition, the bubbles that collect in the curved length are not subsequently separated, and the action of gravity on the bubbles is not impeded.

The bottom level line of the duct means may have a slope in the liquid flow direction which is substantially negative or zero starting from the downstream end of the curved duct portion.

By means of this disposition, the bubble trap of the invention can be emptied almost completely under gravity.

BRIEF DESCRIPTION OF THE DRAWINGS

An embodiment of the invention is described by way of example with reference to the accompanying drawings, in which.

DETAILED DESCRIPTION

Figure 1:
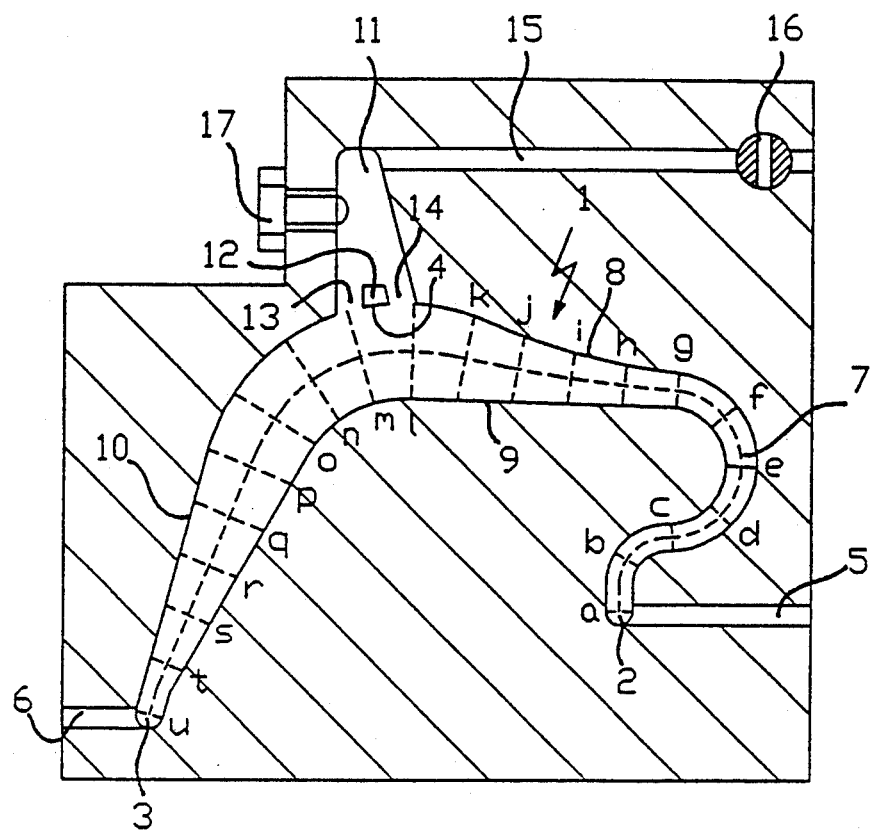
FIG. 1 is a section in a vertical plane through one embodiment of a bubble trap of the invention.

The bubble trap of FIG. 1 includes duct means for the liquid to be degassed and constituted by a channel 1 of varying section having an inlet 2 and an outlet 3 disposed beneath the level of an intermediate settling length that includes a high point 4 where bubbles collect under gravity. The inlet 2 and the outlet 3 are respectively connected to ducts 5 and 6 for connecting to pipework in a hydraulic circuit. The channel 1 is curved at its high point 4.

In accordance with the invention, the channel 1 includes a curved length 7 upstream from the high point 4 with the convex side of the curved length facing outwards, which curved length constitutes means for concentrating bubbles dynamically. The radius of curvature of the length 7 is less than the radius of curvature of the channel 1 at the high point 4. This curved length is of substantially constant section and it runs into the settling length smoothly, the outside curve of the curved length being extended by an upper line 8 of greater slope that terminates at the high point 4 of the settling length. Starting from the downstream end of the curved length 7, the section of the channel 1 increases progressively and becomes substantially constant on either side of the high point 4, after which it decreases progressively down to the outlet 3, which is situated below the level of the inlet 2 and which is of substantially the same section as the inlet 2. The channel 1 is shaped to follow the streamlines of the liquid leaving the curved length 7, thus giving rise to a small amount of convexity facing the inside of the channel 1 for the top line 8 of greatest slope between the downstream end of the curved length 7 and the high point 4. Considered in the liquid flow direction, the slope of the line 9 marking the bottom of the channel 1 from the downstream end of the curved length 7 is substantially zero to a point vertically below the high point 4, after which said slope is negative down to the outlet 3. The angle of the top line 10 of greatest slope in the terminal length of the channel 1 is chosen so that any bubbles that may form on the corresponding wall can move up under gravity along said wall to the high point 4 without any risk of becoming disconnected from the wall or of being entrained by the liquid. Advantageously, this angle lies between about 20° and about 30° relative to the vertical.

Means for collecting gas constituted by an oblong cell 11 having its axis substantially perpendicular to the axis of the channel 1 open out into the settling length in a zone centered approximately on the high point 4 of the channel 1. To prevent eddies occurring at the junction between the cell 11 and the channel 1, the opening to the cell 1 is partially blocked by a partition 12 whose bottom surface extends the top wall of the channel 1, and which delimits two slots 13 and 14 for passing bubbles.

The cell 11 is fitted with purge means constituted by a duct 15 that is closable by means of a valve 16 and that connects the top of the cell to the atmosphere. The valve 16 is controlled on the basis of information provided by a liquid detector 17 disposed halfway up the cell 11.

Figure 2:
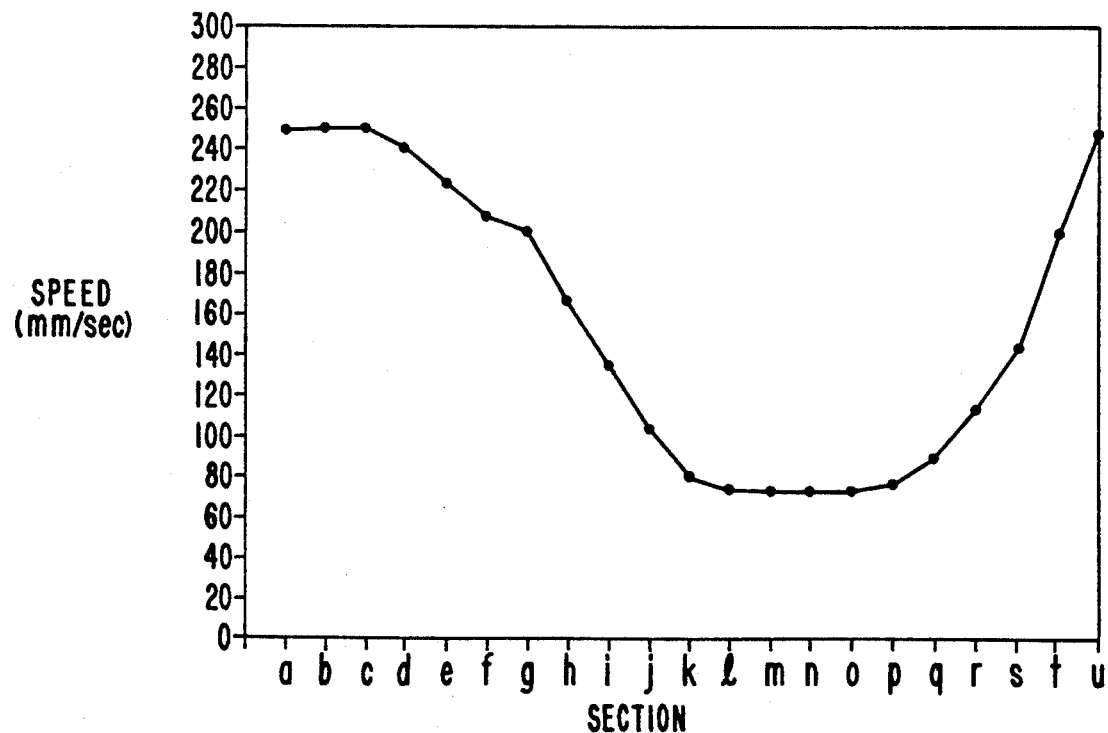
FIG. 2 is a graph showing the mean speed of liquid flow through the FIG. 1 bubble trap.

The graph of FIG. 2 shows that, for constant inlet flow rate, the speed of the liquid begins to drop off only slowly between the inlet 2 (section a) to the downstream end of the curved length 7 (section g) (loss of about 20% of speed), and then more quickly between the section g and the section k, after which the speed is stabilized at about one-third of the inlet speed in a portion of the channel 1 having maximum and constant section (sections k to p), after which the speed increases rapidly beginning from the section q, such that at the outlet 3 (section u) of the bubble trap it has returned to the value it had at the inlet. It may be observed that the bubbles present in the liquid entering the bubble trap are thrust massively towards the outer wall of the curved length 7 such that on leaving said length they remain pressed against the top wall of the channel 1 and slide towards the cell 11 under the effects of gravity and the flow of the liquid. Since the liquid flow has no eddies, the bubbles that are brought together in the curved length remain together. Furthermore, likewise because of the lack of eddies, any bubbles that may have remained inside the stream of liquid settle out under gravity in the settling length where the speed of the liquid is relatively low. They collect against the top wall of the channel 1 on either side of the opening to the cell 11 and they slide therein (solely under the effect of gravity for bubbles downstream from the cell 11) so that they end up accumulating therein. As the cell 11 fills with gas, the level of liquid in the cell 11 moves down until the detector 17 no longer detects the presence of liquid. The valve 16 is then opened and the gas present in the cell 11 is purged, with the level of liquid rising inside the cell, upon which the valve is closed again. Given the shape of the valve 11 which is small in section, the quantity of gas eliminated during each purge is small, and purges are frequent. The flow of liquid through the bubble trap is not disturbed thereby.

A bubble trap like the trap shown lifesize in FIG. 1, having a channel 1 of rectangular right cross-section of width 2.5 cm has a volume of about 40 ml, which is about one-fourth the volume of a conventional bubble trap. With a liquid flow rate of about 1200 ml per minute it enables about 4.5 ml of gas (measured at atmospheric pressure) to be extracted from the liquid per minute, i.e. the same quantity of gas as a conventional bubble trap.

By delivering a gas under pressure via the duct 5 into the bubble trap 1 while full of liquid, it is possible to empty the bubble trap completely.

The present invention is not limited to the embodiment described above, and variants may be provided.

We claim:

1. A device for eliminating bubbles of gas from a liquid, the device comprising:

curved duct means for conveying the liquid, the duct means including an inlet end at an upstream location thereof, an outlet end at a downstream location thereof, a high point in a top wall of the duct means between the inlet and outlet ends for enabling the bubbles to collect by gravity, a portion of flaring diverging section in the duct means upstream of the high point of the top wall, and a portion of tapering converging section in the duct means downstream of the high point of the top wall, the flaring diverging section including the top wall;

means, located in the duct means upstream of the flaring diverging section, for dynamically concentrating the bubbles in an outer upper peripheral region of the duct means, the concentrating means including a curved portion of substantially constant cross-section having a radius of curvature sized so that bubbles of gas move to the top wall of the flaring diverging section as the bubbles exit the concentrating means; and means, extending from the outer peripheral region of the duct means proximate the high point of the top wall, for collecting bubbles from the liquid the collecting means including a gas outlet.

2. A device according to claim 1, wherein the duct means further includes means for substantially preventing eddies in the liquid flowing therethrough.

3. A device according to claim 1, wherein the duct means has a first radius of curvature proximate the high point of the top wall, and the means for dynamically concentrating bubbles has a radius of curvature that is less than the first radius of curvature.

4. A device according to claim 3, wherein the curved portion of the bubble concentrating means defines an outer curved trajectory for the bubbles that runs into a top path of greatest slope in the duct means, which top path terminates at the high point of the top wall.

5. A device according to claim 1, further including bubble collecting means having an oblong cell opening extending from the duct means at the high point of the top wall.

6. A device according to claim 5, wherein the eddy preventing means includes a partition at a junction between the duct means and the cell, the partition providing continuity to the duct means and including at least one slot for passing bubbles.

7. A device according to claim 2, wherein the eddy preventing means includes a portion that follows a profile of the duct means and is shaped to conform to liquid streamlines leaving the bubble concentrating means.

8. A device according to claim 3, wherein a bottom level line of the duct means has a slope in a liquid flow direction which is substantially negative or zero starting from the downstream end of the curved duct portion.

9. A device according to claim 8, wherein the slope of the bottom level line is initially substantially zero until a point approximately vertically below the high point, after which it is negative.

10. A device according to claim 1, wherein an angle of greatest slop of the top wall is in the range about 20° to about 30° relative to vertical.

11. A device according to claim 1, wherein the duct means is of substantially equal cross-section at the inlet and at the outlet thereof.

12. A device according to claim 1, wherein the outlet of the duct means is situated at a lower level than the inlet thereof.

13. A device according to claim 1, including purge means having a closable channel connecting the high point of the collection means to the atmosphere.

14. A device according to claim 13, including a liquid presence detector for detecting the presence of liquid in the bubble collecting means, the purge means being designed for activation when the detector detects an absence of liquid.

15. A device according to claim 1, having a volume of about 40 ml and being sized to enable about 4.5 ml of gas to be extracted from the liquid per minute, with a liquid flow rate of about 1200 ml per minute.

16. A device for eliminating bubbles of gas from a liquid, the device comprising:

curved duct means for conveying the liquid, the duct means including an inlet end at an upstream location thereof, an outlet end at a downstream location thereof, a high point in a top wall of the duct means between the inlet and outlet ends for enabling the bubbles to collect by gravity, a portion of flaring diverging section in the duct means upstream of the high point of the top wall, and a portion of tapering converging section in the duct means downstream of the high point of the top wall, the flaring diverging section including the top wall;

means, located in the duct means upstream of the flaring diverging section, for dynamically concentrating the bubbles in an outer upper peripheral region of the duct means, the concentrating means including a curved portion of substantially constant cross-section having a radius of curvature sized so that bubbles of gas move to the top wall of the flaring diverging section as the bubbles exit the concentrating means; and means, extending from the outer peripheral region of the duct means proximate the high point of the top wall, for collecting bubbles from the liquid the collecting means including a gas outlet, a receptacle for collecting gas connected to the gas outlet, and valve means for selectively permitting collected gas to exit the receptacle.

* * * * *

UNITED STATES PATENT AND TRADEMARK OFFICE
CERTIFICATE OF CORRECTION

PATENT NO. : 5,228,889
DATED : July 20, 1993
INVENTOR(S) : Jean-Loup Cortial, et. al.

It is certified that error appears in the above-indentified patent and that said Letters Patent is hereby corrected as shown below:

Col. 5, claim 10, line 2, change "slop" to --slope--.

Signed and Sealed this

Fifteenth Day of March, 1994

Attest:

BRUCE LEHMAN

Attesting Officer    Commissioner of Patents and Trademarks